United States Patent [19]

Dunn

[11] 4,072,388
[45] Feb. 7, 1978

[54] ANTI-SNAG DEVICE FOR ELECTRODE LEAD CLIPS

[75] Inventor: David M. Dunn, Menomonee Falls, Wis.

[73] Assignee: Marquette Electronics, Inc., Milwaukee, Wis.

[21] Appl. No.: 785,074

[22] Filed: Apr. 6, 1977

[51] Int. Cl.² .............................................. H01R 13/58
[52] U.S. Cl. ........................... 339/103 R; 128/2.06 G; 339/224; 339/261
[58] Field of Search ..................... 128/2.05 D, 2.05 M, 128/2.05 Q, 2.06 R, 2.06 A, 2.06 G, 2.06 V; 339/103 R, 103 C, 103 B, 101, 105, 107, 224, 228, 261

[56] References Cited

U.S. PATENT DOCUMENTS

| 1,698,379 | 1/1929 | Taylor | 339/261 |
| 3,008,114 | 11/1961 | Adkins | 339/228 X |
| 3,129,373 | 4/1964 | Godshalk et al. | 339/224 X |
| 3,951,504 | 4/1976 | Clark | 339/103 R |

Primary Examiner—Roy Lake
Assistant Examiner—DeWalden W. Jones
Attorney, Agent, or Firm—Andrus, Sceales, Starke & Sawall

[57] ABSTRACT

An anti-snag device for use with an electrocardiographic electrode lead clip having moveable arms for engaging the electrode. A lead wire extends from one of the arms. The anti-snag device comprises an elongated means extending from the other arm and joined to the lead wire so as to provide a smoothed configuration to the lead clip. The anti-snag device may comprise a piece of tubing, one end of which is inserted over the arm of the lead clip and the other end of which is fastened to the wire. The anti-snag device may also comprise an integral extension of the arm.

8 Claims, 3 Drawing Figures

ANTI-SNAG DEVICE FOR ELECTRODE LEAD CLIPS

BACKGROUND OF THE INVENTION — FIELD OF THE INVENTION

The present invention relates to an anti-snag device for use with electrocardiographic lead clips.

BACKGROUND OF THE INVENTION — DESCRIPTION OF THE PRIOR ART

The electrical phenonema associated with the physiological functioning of the heart is obtained by electrodes applied to the skin. The electrodes comprise a plate or cup which contacts the skin and a terminal on the exposed side thereof. The terminal may be connected to a lead clip having wires leading to the electrocardiograph. The lead clip typically has a pair of relatively movable, semi-circular segments which embrace the terminal. The segments are opened by squeezing together arms extending from the segments. The lead wire may run through one of the arms to the electrocardiograph.

In the past, lead clips of this type have proven troublesome. A plurality of electrodes, applied relatively close together on the patient's chest, are used in certain types of electrocardiographic analysis. The lead wires and clips leading to the various electrodes tend to become tangled and snag each other. This is due, in great measure, to the projection of the free end of the arm not containing the lead wire. The entanglement of the clips and wires may cause one or more of the electrodes to be removed from the chest or break the connection between a clip and an electrode. The snarl of wires and clips also makes detachment of the clips from the combination of electrodes and reconnection to another combination difficult.

SUMMARY OF THE PRESENT INVENTION

The present invention is directed to an anti-snag device for clip-on electrodes which overcomes the problems heretofore encountered with the use of such elements. The device comprises an elongated means extending from the free end of the lead clip arm not containing the lead wire. The elongated means engages the lead wire at a point sufficiently removed from the free-end of the arm containing the wire as to permit relative movement of the arms when the arms are squeezed. A smooth, non-snagging configuration is thus provided to the lead clip.

In one embodiment of the invention, the elongated means may comprise a piece of plastic tubing having one end slid over the lead clip arm and having a hole in the other end through which the lead wire extends. In another embodiment of the invention the elongated means may comprise an integral extension of the arm not containing the lead wire having a loop for engaging the lead wire.

DETAILED DESCRIPTION OF THE PREFERRED EMBODIMENT

Figure 1:
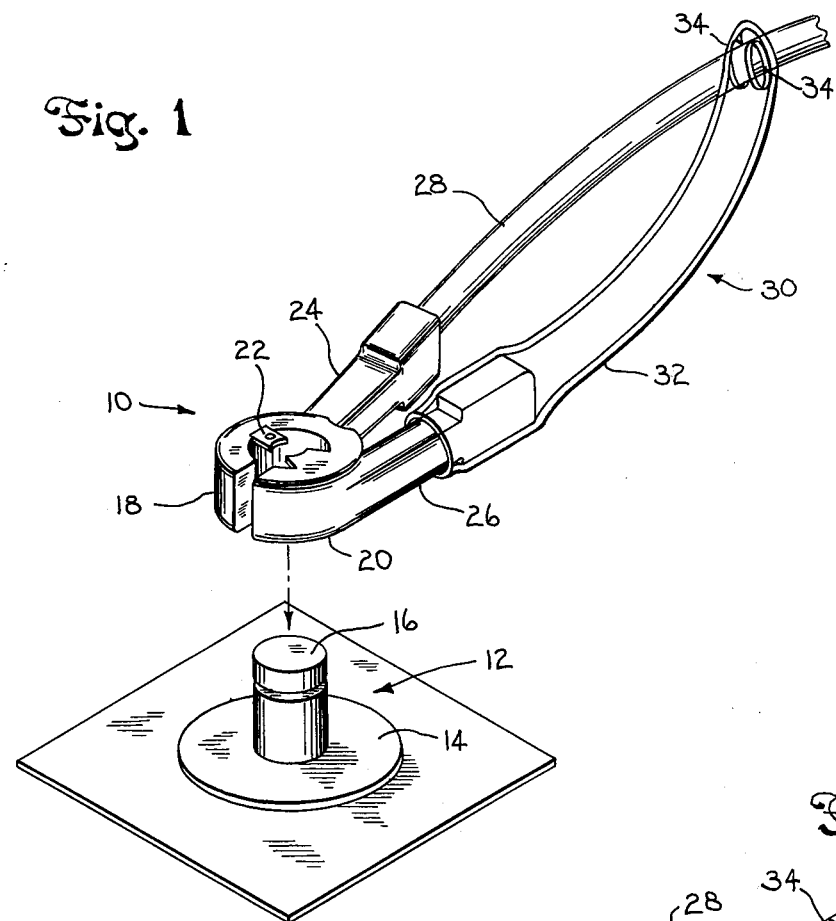
FIG. 1 is a perspective view on one embodiment of the anti-snag device for lead clips of the present invention.
Figure 2:
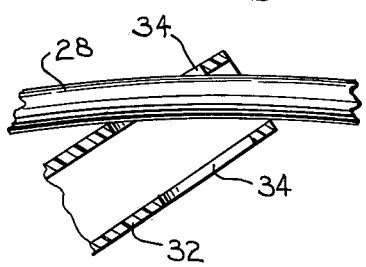
FIG. 2 is a fragmentary enlarged view, partially in cross section, showing a technique for attaching the anti-snag device to the lead wire.

Turning now to FIG. 1, there is shown therein lead clip 10. Lead clip 10 is suitable for use with electrode 12 having a plate 14, which is placed on the patient's skin, and a terminal 16. Lead clip 10 has a pair of generally semicircular segments 18 and 20, at least one of which contains electrical contact 22 for terminal 16. Lead clip 10 may be formed of a resilient plastic material which enables segments to assume the circular position shown in FIG. 1, to embrace terminal 16 when segments 18 and 20 surround terminal 16, and to be spread apart when attaching or removing lead clip 10.

To move segments 18 and 20, a pair of adjacent arms, 24 and 26, are mounted on segments 18 and 20, respectively. Lead wire 28 extends from the contact 22 in segment 18 through arm 24 and exits at the free end of arm 24 for connection to the electrocardiograph.

Anti-snag device 30 of the present invention comprises an elongated means extending from the free end of arm 26 and engaging lead wire 28 at a point removed from the free end of the arm 24. As shown in FIG. 1, anti-snag device 30 may comprise a piece of tubing 32 having one end slid over the free end of arm 26 and having a hole 34 in the other end through which lead wire 28 extends. In a typical embodiment of the invention the plastic tube forming anti-snag device 30 may be 2 inches in length. The tubing is sufficiently flexible so as not to interfere with the movement of arm 26 when lead clip 10 is operated and may be formed of polyethylene. A pair of diametrically opposed holes 34 may be provided in the end of tubing 32, as shown in FIG. 3, to facilitate their formation.

Figure 3:
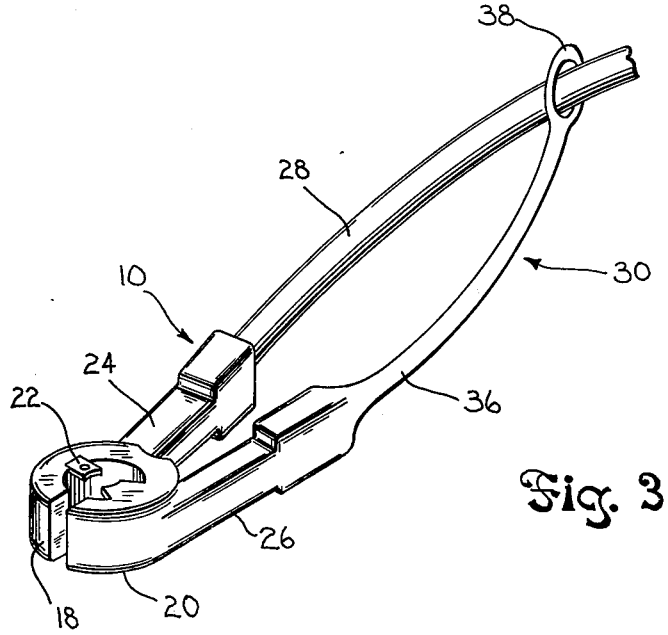
FIG. 3 is a perspective view of another embodiment of the anti-snag device of the present invention.

FIG. 3 shows another embodiment of the anti-snag device 10 of the present invention. In this embodiment, anti-snag device 10 comprises an elongated extension 36 of arm 22 having means engaging lead wire 28. Such a means may comprise a loop 38 which engages the lead wire.

Various modes of carrying out the invention are contemplated as being within the scope of the following claims particularly pointing out and distinctly claiming the subject matter which is regarded as the invention.

I claim:

1. An anti-snag device for use with a lead clip having an electrical contact portion for engaging an electrocardiographic electrode, said electrical contact portion having first and second generally adjacent arms, each of said arms having one end fixed to said electrical contact portion and a free end, said arms being moveable toward and away from each other for opening and closing the clip, said first arm having a lead wire extending from the free end thereof, said anti-snag device comprising:

elongated means extending from the free end of said second arm and engaging said lead wire at a point removed from the free end of said first arm, said elongated means having sufficient length to permit said toward and away movement of said arms.

2. The anti-snag device according to claim 1 wherein the end of said elongated means that engages said lead wire contains a hole through which said lead wire extends.

3. The anti-snag device according to claim 1 wherein the end of said elongated means that engages said lead wire includes a loop for engaging said lead wire.

4. The anti-snag device according to claim 1 wherein said elongated means comprises an integral extension of said second arm.

5. The anti-snag device according to claim 1 wherein said elongated means loosely engages said lead wire.

6. The anti-snag device according to claim 5 wherein said elongated means comprises a tube having one end engaging the free end of said second arm and the other arm engaging said lead wire.

7. The anti-snag device according to claim 1 wherein said elongated means is flexible to facilitate the toward and away movement of said arms.

8. The anti-snag device according to claim 7 wherein one end of said tube is slid over the free end of second arm.

* * * * *